(12) United States Patent
Ramsdell et al.

(10) Patent No.: US 9,280,888 B2
(45) Date of Patent: Mar. 8, 2016

(54) SYSTEMS AND METHODS OF NOTIFYING A PATIENT TO TAKE MEDICATION

(71) Applicant: Time Warner Cable Enterprises LLC, New York, NY (US)

(72) Inventors: Scott W. Ramsdell, Charlotte, NC (US); Susan A. Waxenberg, New York, NY (US)

(73) Assignee: Time Warner Cable Enteprises LLC, New York, NY (US)

( * ) Notice: Subject to any disclaimer, the term of this patent is extended or adjusted under 35 U.S.C. 154(b) by 299 days.

(21) Appl. No.: 13/875,597

(22) Filed: May 2, 2013

(65) Prior Publication Data
US 2014/0327544 A1  Nov. 6, 2014

(51) Int. Cl.
G08B 23/00   (2006.01)
G08B 21/24   (2006.01)
G06F 19/00   (2011.01)

(52) U.S. Cl.
CPC ............ G08B 21/24 (2013.01); G06F 19/3456 (2013.01)

(58) Field of Classification Search
CPC ..................................................... G08B 21/22
USPC ........ 340/309.16, 573.1, 572.1; 600/300, 301
See application file for complete search history.

(56) References Cited

U.S. PATENT DOCUMENTS

| | | | |
|---|---|---|---|
| 6,579,231 B1 * | 6/2003 | Phipps .......................... | 600/300 |
| 2001/0028308 A1 * | 10/2001 | De La Huerga ........... | 340/573.1 |
| 2002/0149473 A1 * | 10/2002 | Romano et al. .......... | 340/309.15 |
| 2008/0154099 A1 * | 6/2008 | Aspel et al. ................... | 600/301 |
| 2009/0167531 A1 * | 7/2009 | Ferguson .................... | 340/572.1 |

* cited by examiner

Primary Examiner — Benjamin C Lee
Assistant Examiner — Israel Daramola
(74) Attorney, Agent, or Firm — Chapin IP Law, LLC (57) ABSTRACT

Systems and methods of scheduling and sending notifications to, and receiving acknowledgements from, patients regarding specific health care events, such as the taking of medications at scheduled times and in prescribed dosages. By directing a patient to take their prescribed dosages of medication at scheduled times based on a schedule of medications prepared for the patient by a health care provider, a caregiver, etc., and enabling the patient to provide acknowledgements of having taken their prescribed dosages of medication, improved health care outcomes can be achieved. Further, by allowing the patient to receive such directives to take their medication, as well as to send such acknowledgements, using a set top box connected to a television set, a mobile device such as a mobile phone, and/or a patient notification device such as a wireless pendant, desired improvements in health care outcomes can be achieved with an increased level of convenience.

20 Claims, 3 Drawing Sheets

SYSTEMS AND METHODS OF NOTIFYING A PATIENT TO TAKE MEDICATION

BACKGROUND

In recent years, significant advances have been made in the development and availability of a variety of medications for treating a wide range of patient illnesses, diseases, and disabilities. As a result, health care providers have, in general, been prescribing medications to more patients than ever before. In order for such medications to be most safe and effective, it is incumbent upon patients to take their prescribed medications at the proper times and in the proper dosages. However, it has become increasingly common for many patients to fail to adhere to a strict medical regimen, particularly with regard to the taking of prescribed medications.

For example, many able-bodied patients lead busy lives that are filled with work, meetings, travel, and family obligations, making compliance to a regular medication schedule difficult, if not virtually impossible. Children and elderly patients can have even more difficulty complying with their regular medication schedules. For example, health care providers frequently prescribe a number of medications to their elderly patients, who may, at times, forget or at least become confused with regard to what medications to take, as well as when to take them. Further, children are often prescribed medications that must be taken during the busy school day, or some time after school when they may be involved in sports or other after-school activities that can distract them from their regular medication schedules.

BRIEF DESCRIPTION OF EMBODIMENTS

In accordance with the present application, systems and methods are disclosed for scheduling and sending notifications to, and receiving acknowledgements from, patients with regard to specific health care events, such as the taking of medications at scheduled times and in prescribed dosages. The disclosed systems and methods allow patients to receive directives to take medication, as well as send acknowledgements of having taken their medication, using, e.g., a set top box connected to a television set or other display device, a mobile device such as a mobile phone, a patient notification device such as a wireless pendant, etc., thereby providing improved health care outcomes with an increased level of convenience.

In one aspect, the disclosed system (also referred to herein as the "patient notification system") includes a scheduling server, an authentication server, a notification server, and an account information database. The scheduling server is communicably connectable, via a public network such as the Internet, to at least one computerized device of a health care provider, a caregiver, or any other suitable individual, such as a smartphone, or a desktop, laptop, or tablet computer. The notification server is communicably connectable to at least one mobile device via the Internet or a wireless telecommunications network, and at least one network access device via a video services network. For example, the network access device may be a set top box connected to a television set or other display device, and the video services network may be a cable television (CATV) network or an Internet protocol television (IPTV) network. The notification server is also communicably connectable, via an intelligent home network, to an intelligent home gateway, which, in turn, is communicably connected to a patient notification device, such as a wireless pendant.

In an exemplary mode of operation, the health care provider, the caregiver, etc., can employ his or her computerized device to securely access the scheduling server within the patient notification system over the Internet. For example, the health care provider, the caregiver, etc., may securely access the scheduling server through a webpage or software application running on the computerized device, and provide credentials such as a username/password combination that verifies him or her to the scheduling server, as well as a patient account number that allows him or her to prepare a personalized schedule of medications for a particular patient via the webpage or software application.

Once the health care provider, the caregiver, etc., is verified to the scheduling server and the patient's schedule of medications is completed, the scheduling server establishes a secure connection to the authentication server, and directs the authentication server to query the account information database to obtain personalized information pertaining to one or more patient notification devices associated with the patient account number. For example, the patient notification devices may include the set top box, the mobile device, the wireless pendant, and/or any other suitable wired or wireless device. Further, the personalized information pertaining to the patient notification devices may include a unique identification code designed to avoid direct association of the personalized information with the patient, as well as a list of reference numbers, device types, and addressable information for the respective notification devices. The authentication server securely sends the unique identification code and the list of reference numbers to the scheduling server, and securely sends the unique identification code, the list of reference numbers, the device types, and the addressable information for the respective notification devices to the notification server.

The schedule of medications prepared for the patient by the health care provider, the caregiver, etc., may include information pertaining to one or more health care events, such as times during one or more 24-hour periods when prescribed dosages of one or more medications are to be taken by the patient. Upon completion of the schedule of medications, or at any other suitable time, the scheduling server processes the schedule of medications, and, based on that schedule of medications, monitors for a health care event to occur, such as the detection of a time during a 24-hour period when the patient is scheduled to take a prescribed dosage of medication.

Once the scheduled time for taking the prescribed dosage of medication is detected, the scheduling server securely sends, to the notification server, a message including the unique identification code and the list of reference numbers for the respective notification devices associated with the patient. The notification server processes the message from the scheduling server to determine the device types for the respective notification devices, based at least on the unique identification code and the list of reference numbers contained in the message.

In the event the device types for the patient notification devices include the set top box, the notification server securely sends a notification message to the set top box via the video services network, using the addressable information for the set top box provided by the authentication server. Further, a software application running on the set top box monitors for receipt of such a notification message, and, in response to the receipt of the notification message, causes a corresponding video and/or audio notification to be presented on the television set or other display device connected thereto. For example, the set top box may cause the television set or display device to visibly and/or audibly present the notification, "It is now time for Doris to take one 20 mg tablet of cholesterol-lowering medication". After the patient, Doris, takes the prescribed dosage of medication, she provides an acknowledgement of having taken the medication to the notification server. For example, the patient, Doris, may employ a remote control device to send a specified acknowledgement signal to the set top box, which, in turn, securely forwards Doris's acknowledgement of having taken the medication to the notification server over the video services network.

In the event the device types for the patient notification devices further include the mobile device, the notification server can securely send a notification message to the mobile device via the Internet or the wireless telecommunications network, using the addressable information for the mobile device provided by the authentication server. Further, a software application running on the mobile device monitors for receipt of such a notification message, and, in response to the receipt of the notification message, causes a corresponding video and/or audio notification to be presented on the mobile device. For example, the mobile device may visibly and/or audibly present the same or similar notification, "It is now time for Doris to take one 20 mg tablet of cholesterol-lowering medication". If she has not already done so, the patient, Doris, can provide her acknowledgement of having taken the medication to the notification server using the mobile device, securely sending a specified message of acknowledgment to the notification server over the Internet or the wireless telecommunications network.

In the event the device types for the patient notification devices further include the wireless pendant, the notification server can securely send a notification message to the intelligent home gateway via the intelligent home network, using the addressable information for the intelligent home gateway provided by the authentication server. Further, a software application running on the intelligent home gateway monitors for receipt of such a notification message, and, in response to the receipt of the notification message, causes a corresponding visible, audible, and/or vibration notification to be presented on the wireless pendant. For example, the wireless pendant may visibly and/or audibly present the same or similar notification, "It is now time for Doris to take one 20 mg tablet of cholesterol-lowering medication". If she has not already done so, the patient, Doris, can provide an acknowledgement of having taken the medication to the notification server using either the wireless pendant or the intelligent home gateway, securely sending a specified message of acknowledgment to the notification server over the intelligent home network.

Having received the patient acknowledgement provided by the set top box, the mobile device, or the wireless pendant/intelligent home gateway, the notification server securely forwards the acknowledgement to the scheduling server, which securely records the acknowledgement in memory and/or any other suitable data storage. The notification server may also securely forward the patient acknowledgement to the computerized device of the health care provider, the caregiver, etc., over the Internet for secure storage in association with the computerized device.

In the event the notification server does not receive an acknowledgement from the patient within a predetermined time period, the notification server can notify the scheduling server and/or the computerized device of the health care provider, the caregiver, etc., of its failure to receive the patient acknowledgement. Further, the scheduling server, the computerized device of the health care provider, the caregiver, etc., and/or the health care provider or caregiver himself/herself can take appropriate steps in response to the failure to receive the patient acknowledgement. For example, the scheduling server or the computerized device of the health care provider, the caregiver, etc., can send, via the notification server, an emergency message to the set top box, the mobile device, the wireless pendant, and/or to a specified telephone number to alert emergency services. At a desired time, the health care provider, the caregiver, etc., can employ his or her computerized device to securely access the scheduling server to obtain a report of the various notifications sent to, as well as the corresponding acknowledgements received from, his or her patient.

By directing a patient to take one or more specified actions, such as the taking of one or more prescribed dosages of medication at one or more scheduled times based on a schedule of medications prepared for the patient, and enabling the patient to provide acknowledgements of having taken their prescribed dosages of medication, improved health care outcomes can be achieved. Further, by allowing the patient to receive such directives to take medication as well as send acknowledgements of having taken their medication using a set top box connected to a television set, a mobile device such as a mobile phone, and/or a patient notification device such as a wireless pendant, desired improvements in health care outcomes can be achieved with an increased level of convenience.

It is noted that the ordering of various steps and/or actions performed in the exemplary mode of operation described above has been provided for purposes of illustration, and that the various steps/actions as described herein can be performed in any suitable order. It is further noted that other aspects of the present application can include software programs and/or hardware operative to perform any of the steps/actions summarized above and described in further detail below.

It is to be understood that systems, methods, apparatus, instructions on computer readable storage media, etc., as described herein, can be embodied as one or more software programs, firmware, a hybrid of software, hardware, and/or firmware, or hardware alone, such as within one or more processors, operating systems, and/or software applications. It is to be further understood that the various servers described herein, including the scheduling server, the authentication server, and/or the notification server within the patient notification system, can be embodied as one or more processes implemented in software, hardware, firmware, or any suitable combination thereof, on one or more computers or any other suitable computerized devices and/or one or more computerized components implemented in software, hardware, firmware, or any suitable combination thereof.

Various techniques described herein are well suited for processing patient notifications. It should be noted, however, that the techniques described herein are not limited to use in such applications, and that the techniques described herein are suited for other applications as well.

In addition, although each of the different features, techniques, configurations, etc., described herein may be discussed in different places within the present application, it is intended, where suitable, that each of these concepts can be executed independently of, or in combination with, each other. Accordingly, the various aspects of the present application, as described herein, can be embodied and viewed in many different ways.

It is noted that this preliminary discussion of the various aspects of the present application does not specify every aspect of the application or claimed invention(s). Rather, this discussion presents general embodiments and corresponding points of novelty over conventional techniques. For further details and/or possible perspectives (permutations) of the claimed invention(s), the reader is directed to the Detailed Description and corresponding drawing figures of the present application, as provided below.

BRIEF DESCRIPTION OF THE DRAWINGS

The accompanying drawings, which are incorporated in and constitute a part of this specification, illustrate one or more embodiments described herein and, together with the Detailed Description, explain these embodiments. In the drawings.

DETAILED DESCRIPTION AND FURTHER SUMMARY OF EMBODIMENTS

Systems and methods are disclosed for scheduling and sending notifications to, and receiving acknowledgements from, patients regarding specific health care events, such as the taking of medications at scheduled times and in prescribed dosages. The disclosed systems and methods can direct a patient to take their prescribed dosages of medication at scheduled times based on a schedule of medications prepared for the patient by a health care provider, a caregiver, or any other suitable individual, and enable the patient to provide acknowledgements of having taken their prescribed dosages of medication, thereby improving overall health care outcomes. The disclosed systems and methods also allow the patient to receive such directives to take medication, as well as send acknowledgements of having taken the medication, using a set top box connected to a television set, a mobile device such as a mobile phone, and/or a patient notification device such as a wireless pendant, thereby allowing desired improvements in health care outcomes to be achieved with an increased level of convenience.

Figure 1:
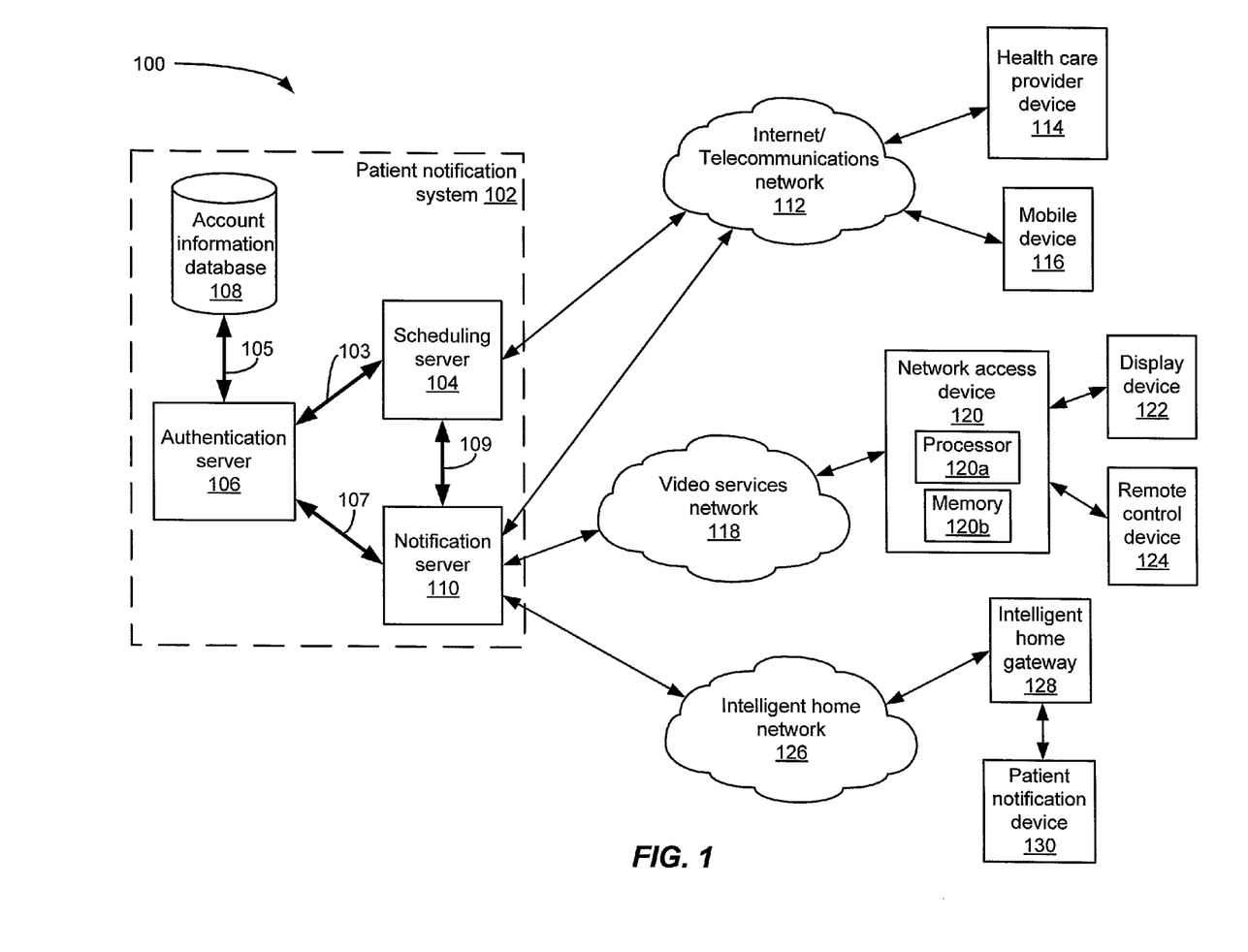
FIG. 1 is a diagram of an exemplary environment in which an exemplary patient notification system may be employed, in accordance with the present application.

FIG. 1 depicts an exemplary environment 100 in which an illustrative embodiment of a patient notification system 102 may be employed, in accordance with the present application. As shown in FIG. 1, the patient notification system 102 includes a scheduling server 104, an authentication server 106, a notification server 110, and an account information database 108. The scheduling server 104 is communicably connectable, via the Internet and/or a wired or wireless telecommunications network 112, to at least one computerized health care provider device 114, such as a smartphone, a desktop computer, a laptop computer, a tablet computer, or any other suitable computerized device. The notification server 110 is communicably connectable to at least one mobile device 116 via the Internet/telecommunications network 112, and at least one network access device 120 via a video services network 118. For example, the mobile device 116 may be a mobile phone or any other suitable mobile device. Further, the network access device 120 may be a set top box or any other suitable network access device connected to a television set or other display device 122. The set top box may be a standalone set top box, or a set top box incorporated into a cable-ready television set, and the display device 122 may be a personal computer or any other suitable display device. The video services network 118 may be a cable television (CATV) network, an Internet protocol television (IPTV) network, or any other suitable network. The notification server 110 is also communicably connectable, via an intelligent home network 126, to an intelligent home gateway 128, which, in turn, is communicably connected to a patient notification device 130, such as a wireless pendant or any other suitable patient notification device, using WIFI or 802.11 based communication, Bluetooth communication, Zigbee communication, or any other suitable wireless communication or combination thereof.

In an illustrative mode of operation, a health care provider can employ the health care provider device 114 to securely access the scheduling server 104 within the patient notification system 102 over the Internet. For example, the health care provider may securely access the scheduling server through a webpage or software application running on the health care provider device 114, and provide credentials such as a username/password combination, or any other suitable credentials, which verify him or her to the scheduling server 104. The health care provider may also provide a patient account number that allows him or her to prepare a personalized schedule of medications for a particular patient via the webpage or software application. It is noted that any other suitable manner of securely accessing the scheduling server 104 from the health care provider device 114 may be employed.

Once the health care provider is verified to the scheduling server 104 and the patient's schedule of medications is completed, the scheduling server 104 establishes a secured connection 103 to the authentication server 106, and directs the authentication server 106 to query the account information database 108 to obtain personalized information pertaining to one or more patient notification devices associated with the patient account number. For example, the secured connection 103 may include a secured authentication network protected with encryption, or any other suitable secured connection/network. Further, the patient notification devices may include the network access device 120 configured as a set top box, the mobile device 116 configured as a mobile phone, the patient notification device 130 configured as a wireless pendant, and/or any other suitable wired or wireless notification device. Moreover, the personalized information pertaining to the patient notification devices may include a unique identification code designed to avoid direct association of the personalized information with the patient, as well as a list of reference numbers, device types, and addressable information for the respective notification devices. Such personalized information of a patient may be stored in the account information database 108 at a time when the patient opts into a notification program implemented by the patient notification system 102.

The authentication server 106 obtains the personalized information associated with the patient account number from the account information database 108 over a secured connection 105, which can include a secured patient billing system network protected with encryption, or any other suitable secured connection/network. The authentication server 106 sends the unique identification code and the list of reference numbers to the scheduling server 104 over the secured connection 103, and sends the unique identification code, the list of reference numbers, the device types, and the addressable information for the respective notification devices to the notification server 110 over a secured connection 107, which, like the secured connection 103, may include the secured authentication network protected with encryption, or any other suitable secured connection/network.

It is noted that the schedule of medications prepared for the patient by the health care provider may include information pertaining to one or more health care events, such as times during one or more 24-hour periods when prescribed dosages of one or more medications are to be taken by the patient. Upon completion of the schedule of medications, or at any other suitable time, the scheduling server 104 processes the schedule of medications, and, based on that schedule of medications, monitors for a health care event to occur, such as the detection of a time during a 24-hour period when the patient is scheduled to take a prescribed dosage of medication.

Once the scheduled time for taking the prescribed dosage of medication is detected, the scheduling server 104 securely sends, to the notification server 110, a message including the unique identification code and the list of reference numbers for the respective notification devices associated with the patient. For example, the scheduling server 104 may send the unique identification code and the list of reference numbers over another secured connection 109, such as a secured services network protected with encryption, or any other suitable secured connection/network. The notification server 110 processes the message from the scheduling server 104 to determine the device types for the respective notification devices, based at least on the unique identification code and the list of reference numbers contained in the message.

As described herein, the device types for the patient notification devices can correspond to the network access device 120 configured as a set top box, the mobile device 116 configured as a mobile phone, and/or the patient notification device 130 configured as a wireless pendant. In the event the patient notification devices include the set top box, the notification server 110 securely sends a notification message to the set top box via the video services network 118, using the addressable information provided by the authentication server 106 and an appropriate protocol for the set top box. For example, the video services network 118 may include a secured set top box network protected with encryption, or any other suitable secured network.

The network access device 120 configured as a set top box includes at least one processor 120a operative to execute at least one software application out of at least one memory 120b to monitor for receipt of such a notification message, and, in response to the receipt of the notification message, to cause a corresponding video and/or audio notification to be presented on the television set or other display device 122 connected thereto. For example, the notification may include text, video, audio, and/or at least one image. Further, the set top box may cause the television set or display device 122 to visibly and/or audibly present a notification, such as, "It is now time for Gus to take one 50 mg tablet of heart medication". After the patient, Gus, takes the prescribed dosage of medication, he provides an acknowledgement of having taken the medication to the notification server 110. For example, the patient, Gus, may employ a remote control device 124 to send a specified acknowledgement signal to the set top box. Further, the remote control device 124 may be configured to employ any suitable infrared (IR) or radio frequency (RF) signal for sending the acknowledgement signal to the set top box. The software application executing within the set top box operates to detect the specified acknowledgement signal from the remote control device 124, and to securely forward Gus's acknowledgement of having taken the medication to the notification server 110, e.g., as an out-of-band signal over the video services network 118.

The scheduling server 104 further processes the schedule of medications, and monitors for another health care event to occur, such as the detection of a time during a 24-hour period when the patient is scheduled to take another prescribed dosage of medication. Once the scheduled time for taking the next prescribed dosage of medication is detected, the scheduling server 104 securely sends, to the notification server 110, another message including the unique identification code and the list of reference numbers for the respective notification devices associated with the patient. The notification server 110 processes the message from the scheduling server 104 to determine the device types for the respective notification devices, based at least on the unique identification code and the list of reference numbers contained in the message.

In the event the patient notification devices further include the mobile device 116, the notification server 110 can securely send a notification message to the mobile device 116 over the Internet/telecommunications network 112, using the addressable information provided by the authentication server 106 and an appropriate protocol for the mobile device 116. Like the set top box, the mobile device 116 is processor-based, and a software application executed by the processor within the mobile device 116 monitors for receipt of such a notification message. In response to the receipt of the notification message, the software application executing within the mobile device 116 causes a corresponding video and/or audio notification to be presented on the mobile device 116. For example, the mobile device may visibly and/or audibly present a notification, such as, "It is now time for Gus to take one 20 mg tablet of cholesterol-lowering medication". After the patient, Gus, takes the prescribed dosage of cholesterol-lowering medication, he can provide his acknowledgement of having taken the medication to the notification server 110 using the mobile device 116, securely sending a specified message of acknowledgment to the notification server 110 over the Internet/telecommunications network 112.

The scheduling server 104 continues to process the schedule of medications, and to monitor for still another health care event to occur, such as the detection of a time during a 24-hour period when the patient is scheduled to take a further prescribed dosage of medication. Once the scheduled time for taking the next prescribed dosage of medication is detected, the scheduling server 104 securely sends, to the notification server 110, a further message including the unique identification code and the list of reference numbers for the respective notification devices associated with the patient. The notification server 110 again processes the message from the scheduling server 104 to determine the device types for the respective notification devices, based at least on the unique identification code and the list of reference numbers contained in the message.

In the event the device types for the patient notification devices further include the wireless pendant, the notification server 110 can securely send a notification message to the intelligent home gateway 128 via the intelligent home network 126, using the addressable information provided by the authentication server 106 and an appropriate protocol for the intelligent home gateway 128. A software application executed by the intelligent home gateway 128 monitors for receipt of such a notification message, and, in response to the receipt of the notification message, causes a corresponding visible, audible, and/or vibration notification to be presented on the wireless pendant. For example, the wireless pendant may visibly and/or audibly present, with or without vibration, a notification, such as, "It is now time for Gus to take one 75 mg tablet of blood-thinning medication". After the patient, Gus, takes the prescribed dosage of medication, he can provide an acknowledgement of having taken the medication to the notification server 110 using the wireless pendant or the intelligent home gateway 128, securely sending a specified message of acknowledgment to the notification server 110 over the intelligent home network 126.

Having received the patient acknowledgements provided by the set top box, the mobile device 116, and/or the wireless pendant/intelligent home gateway 128, the notification server 110 securely forwards each acknowledgement over the secured connection 109 to the scheduling server 104, which securely records the acknowledgement in memory and/or any other suitable data storage. The notification server 110 may also securely forward the patient acknowledgement to the health care provider device 114 over the Internet via e-mail, a push notification, etc., for secure storage in association with the health care provider device 114.

In the event the notification server 110 does not receive an acknowledgement from the patient within a predetermined time period, the notification server 110 can notify the scheduling server 104 and/or the health care provider device 114 of its failure to receive the patient acknowledgement. Further, the scheduling server 104, the health care provider device 114, and/or the health care provider himself/herself can take appropriate steps in response to the failure to receive the patient acknowledgement. For example, the scheduling server 104 or the health care provider device 114 can send an emergency message to the set top box, the mobile device 116, and/or the wireless pendant/intelligent home gateway 128, and/or to a specified telephone number to alert emergency services. At a desired time, the health care provider can employ his or her computerized device 114 to securely access the scheduling server 104 to obtain a report of the various notifications sent to, as well as the corresponding acknowledgements received from, his or her patient.

In the illustrative mode of operating the patient notification system 100 discussed above, it was described that a patient can receive a series of notifications directing him or her to take medication via a set top box, a mobile device, a patient notification device, etc. It is noted that, when opting into the notification program, patients can elect to receive such series of notifications via the same notification device, or a plurality of different notification devices. In the event a patient elects to receive such notifications via multiple different notification devices, such as a television set connected to a set top box, a mobile phone, and/or a wearable pendant, he or she need only provide a single acknowledgement of having taken their prescribed dosage of medication at each scheduled time to the notification server 110, using a selected one of the respective notification devices. The notification server 110 securely forwards that single acknowledgement from the patient over the secured connection 109 to the scheduling server 104, which securely records that acknowledgement in memory and/or other data storage.

It was further described herein that the scheduling server 104, the health care provider device 114, and/or the health care provider himself/herself can take appropriate steps in response to a failure to receive a patient's acknowledgement of having taken a prescribed dosage of medication at a scheduled time. To evaluate the status of such a non-responsive patient, the patient may be provided with one or more wearable wireless pendants that monitor one or more vital statistics of the patient, such as his or her blood pressure, heart rate, respiration, etc. Using WIFI or 802.11 based communication, Bluetooth communication, Zigbee communication, or any other suitable wireless communication, such wireless pendants can provide the patient's blood pressure, heart rate, and/or respiration reading to the intelligent home gateway 128, which can securely forward the respective readings to the notification server 110 over the intelligent home network 126. Any subsequent decisions to alert emergency services can then be based at least in part on the monitored vital statistics of the patient.

In some cases, a patient may be incapacitated to the extent that he or she is not only incapable of providing an acknowledgement of having taken medication, but also incapable of taking their medication by themselves. In one embodiment, the notification server 110 can be configured to send, at one or more scheduled times, one or more signals to trigger a medical device for automatically administering a prescribed dosage of medication to the incapacitated patient. For example, the notification server 110 may send a signal over the Internet/telecommunications network 112, the video services network 118, or the intelligent home network 126, for triggering a medical device operative to administer the prescribed dosage of medication intravenously to the patient. Further, the patient may be provided with one or more wearable wireless pendants that monitor one or more vital statistics of the patient, such as his or her blood pressure, heart rate, respiration, etc., thereby allowing a health care provider to monitor the patient's status in response to having received their medication. In another embodiment, the notification server 110 can be configured to send, at one or more scheduled times, one or more signals over the Internet/telecommunications network 112, the video services network 118, or the intelligent home network 126, to actuate a pill box for dispensing a prescribed dosage of medication to a patient.

Figure 2:
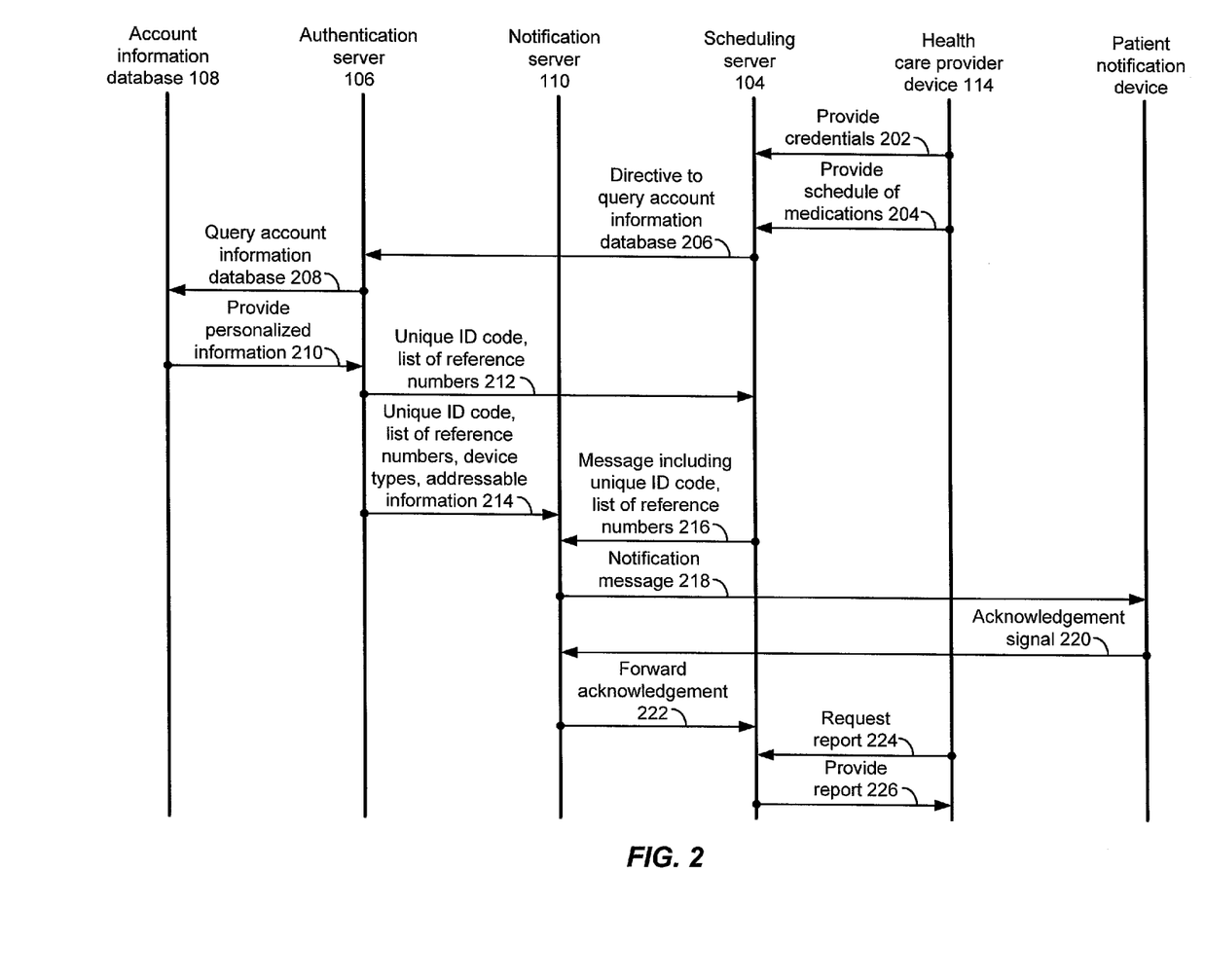
FIG. 2 is a diagram of exemplary signaling and/or messaging between various elements of the patient notification system within the environment of FIG. 1.

Exemplary signaling and/or messaging between the scheduling server 104, the authentication server 106, the notification server 110, and the account information database 108 within the patient notification system 102, as well as between the various elements of the patient notification system 102 and the health care provider device 114 and a patient notification device (e.g., the network access device 120, the mobile device 116, or the wireless pendant/intelligent home gateway 128), is described below with reference to FIG. 2. As shown in FIG. 2, the health care provider device 114 provides credentials that verify a health care provider to the scheduling server 104 (see reference numeral 202). Once the health care provider is verified to the scheduling server 104, the health care provider completes a schedule of medications for at least one patient, and the health care provider device 114 provides the patient's schedule of medications to the scheduling server 104 (see reference numeral 204). The scheduling server 104 directs the authentication server 106 to query the account information database 108 to obtain personalized information pertaining to at least one patient notification device associated with the patient (see reference numeral 206). The authentication server 106 queries the account information database 108 for the requested personalized information (see reference numeral 208), and the account information database 108 provides the personalized information (e.g., a unique identification code, a list of reference numbers, device types, and addressable information for the patient notification device(s)) to the authentication server 106 (see reference numeral 210). The authentication server 106 sends the unique identification code and the list of reference numbers to the scheduling server 104 (see reference numeral 212), and sends the unique identification code, the list of reference numbers, the device types, and the addressable information for the respective notification device to the notification server 110 (see reference numeral 214).

Upon detection of a scheduled time for taking a prescribed dosage of medication, the scheduling server 104 sends, to the notification server 110, a message including the unique identification code and the list of reference numbers for the patient notification device associated with the patient (see reference numeral 216). The notification server 110 sends a notification message to the patient notification device using the addressable information for that notification device (see reference numeral 218), directing the patient to take their prescribed dosage of medication. In response to receipt of the notification message, the patient notification device presents a corresponding video, audio, and/or vibration notification on the respective notification device. Once the patient takes the prescribed dosage of medication, the patient operates the patient notification device to send a specified acknowledgement signal to the notification server 110, indicating that he or she has taken their medication (see reference numeral 220). The notification server 110 forwards the patient acknowledgement to the scheduling server 104, which records the acknowledgement in memory and/or any other suitable storage (see reference numeral 222). At a desired time, using the health care provider device 114, the health care provider requests, from the scheduling server 104, a report of the various notifications sent to, as well as the corresponding acknowledgements received from, his or her patient (see reference numeral 224). In response to the health care provider's request, the scheduling server 104 provides the report to the health care provider device 114 (see reference numeral 226).

Figure 3:
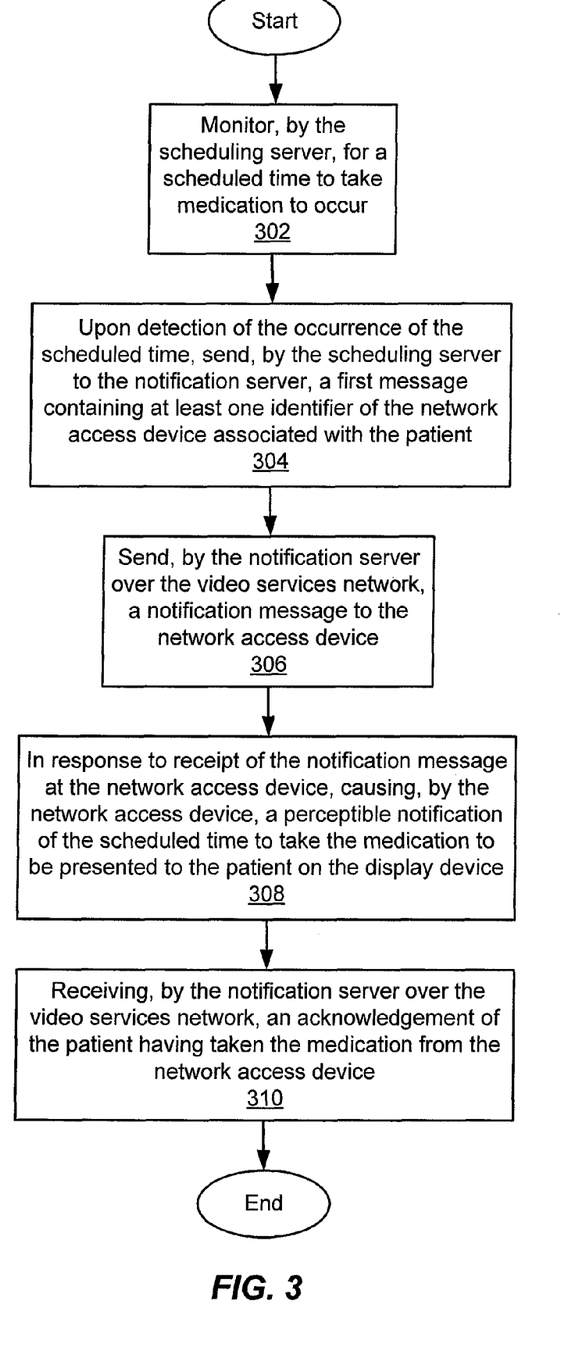
FIG. 3 is a flow diagram of an exemplary method of operating the patient notification system of FIG. 1.

A method of operating the disclosed personal notification system 102 is described below with reference to FIGS. 1 and 3. As depicted in block 302, the scheduling server 104 monitors for a scheduled time to take medication to occur. As depicted in block 304, upon detection of the occurrence of the scheduled time, the scheduling server 104 sends, to the notification server 110, a first message containing at least one identifier of the network access device 120 associated with the patient, in which the network access device 120 is communicably connectable to the display device 122. As depicted in block 306, the notification server 110 sends, over the video services network 118, a notification message to the network access device 120. As depicted in block 308, in response to receipt of the notification message at the network access device 120, the network access device 120 causes a perceptible notification of the scheduled time to take the medication to be presented to the patient on the display device 122. As depicted in block 310, the notification server 110 receives, over the video services network 118, an acknowledgement of the patient having taken the medication from the network access device 120.

In the above detailed description of the disclosed patient notification systems and methods, numerous specific details have been set forth to provide a thorough understanding of claimed subject matter. However, it will be understood by those skilled in the art that such claimed subject matter may be practiced without these specific details. In other instances, methods, apparatus, systems, etc., that would be known by one of ordinary skill in the art have not been described in detail so as not to obscure the claimed subject matter. Some portions of the detailed description have been presented in terms of algorithms or symbolic representations of operations on information, data, and/or signals stored within memory, such as a computer memory. These algorithmic descriptions or representations are examples of techniques used by those of ordinary skill in the data processing arts to convey the substance of their work to others skilled in the art. An algorithm as described herein, and generally, is considered to be a self-consistent sequence of operations or similar processing steps leading to a desired result. In this context, such operations or processing steps involve physical manipulation of physical quantities. Typically, although not necessarily, such quantities may take the form of electrical or magnetic signals capable of being stored, transferred, combined, compared, or otherwise manipulated. It has been convenient at times, principally for reasons of common usage, to refer to such signals as bits, data, values, elements, symbols, characters, terms, numbers, numerals, or the like. It should be understood, however, that all of these and similar terms are to be associated with appropriate physical quantities and are merely convenient labels. Unless specifically stated otherwise, it is appreciated that throughout this specification discussions utilizing terms such as "processing", "computing", "calculating", "determining", or the like refer to actions or processes of a computing platform, such as a computer or a similar electronic computing device, that manipulates or transforms data represented as physical electronic or magnetic quantities within memories, registers, or other information storage devices, transmission devices, or display devices of the computing platform.

While this invention has been particularly shown and described with references to preferred embodiments thereof, it will be understood by those skilled in the art that various changes in form and details may be made therein without departing from the spirit and scope of the present application, as defined by the appended claims. Such variations are intended to be covered by the scope of this present application. As such, the foregoing description of embodiments of the present application is not intended to be limiting. Rather, any limitations to the invention are presented in the following claims.

What is claimed is:

1. A method of providing one or more notifications to, and receiving one or more acknowledgements from, a patient with regard to taking medication at least one scheduled time, comprising:

in response to the patient opting-in to a notification program:

obtaining personalized information pertaining to the patient, the personalized information including (1) a unique identification code for the patient, (2) a predetermined reference number for each of at least one network access device associated with the patient, and (3) addressable information for the network access device, the network access device being communicably connectable to a display device, the opting-in of the patient to the notification program including electing to receive the one or more notifications via the network access device; and storing the personalized information in an account information database;

obtaining, by a computerized authentication component, the personalized information from the account information database;

securely providing, by the computerized authentication component, (1) the unique identification code for the patient, (2) the predetermined reference number for the network access device, and (3) the addressable information for the network access device, to a computerized notification component;

securely providing, by the computerized authentication component, (1) the unique identification code for the patient, and (2) the predetermined reference number for the network access device, to a computerized scheduling component;

monitoring, by the computerized scheduling component, for the scheduled time to take the medication to occur;

upon detection of the occurrence of the scheduled time, securely sending, by the computerized scheduling component to the computerized notification component, a first message containing (1) the unique identification code for the patient, and (2) the predetermined reference number for the network access device associated with the patient;

upon receipt of the unique identification code and the predetermined reference number from the computerized scheduling component, securely sending, by the computerized notification component over at least one network, a notification message to the network access device in accordance with the addressable information for the network access device;

in response to receipt of the notification message at the network access device, causing, by the network access device, a perceptible notification of the scheduled time to take the medication to be presented to the patient on the display device; and receiving, at the computerized notification component over the at least one network, an acknowledgement of the patient having taken the medication from a selected one of the at least one network access device;

wherein the network access device is a set top box, wherein the at least one network includes one or more of a cable television (CATV) network and an Internet protocol television (IPTV) network, and wherein the sending of the notification message includes sending the notification message to the set top box over one or more of the CATV network and the IPTV network.

2. The method of claim 1, further comprising:
monitoring, by the set top box, for the receipt of the notification message.

3. The method of claim 2 wherein the causing of the perceptible notification to be presented on the display device includes causing, by the set top box, one or more of a text notification, a video notification, an audio notification, and an image notification to be presented to the patient on the display device.

4. The method of claim 1 further comprising:
sending, by a remote control device, at least one signal indicative of the acknowledgement of the patient having taken the medication to the network access device.

5. The method of claim 4 wherein the sending of the at least one signal to the network access device includes sending, by the remote control device, one or more of an infrared signal and a radio frequency signal indicative of the acknowledgement of the patient having taken the medication.

6. The method of claim 1 further comprising:
receiving, at the computerized scheduling component from at least one computerized device, credentials of at least one specified individual for use in verifying the specified individual to the computerized scheduling component.

7. The method of claim 6 further comprising:
receiving, at the computerized scheduling component from the computerized device, a patient account number for use in allowing the specified individual to prepare a schedule of medications for the patient on the computerized device.

8. The method of claim 7 further comprising:
receiving, at the computerized scheduling component from the computerized device, the schedule of medications for the patient, the schedule of medications including the scheduled time for the patient to take the medication.

9. The method of claim 8 further comprising:
directing, by the computerized scheduling component, the computerized authentication component to query the account information database for the personalized information pertaining to the patient using the patient account number, the personalized information including one or more of the unique identification code designed to avoid direct association of the personalized information with the patient, the predetermined reference number for the network access device, a device type for the network access device, and addressable information for the network access device.

10. The method of claim 9 further comprising:
querying, by the computerized authentication component, the account information database for the personalized information pertaining to the patient.

11. The method of claim 1 further comprising:
forwarding, by the computerized notification component, the acknowledgement of the patient having taken the medication to the computerized scheduling component.

12. The method of claim 11 further comprising:
storing, by the computerized scheduling component, the acknowledgement of the patient having taken the medication in at least one data storage.

13. The method of claim 11 further comprising:
sending, by the computerized scheduling component, at least one report of one or more of the notification message sent to, and the acknowledgement received from, the patient, to at least one computerized device.

14. The method of claim 1 further comprising:
in the event the acknowledgement of the patient having taken the medication is not received at the computerized notification component from the network access device, notifying, by the computerized notification component, one or more of the computerized scheduling component and a computerized device of a specified individual of a failure to receive the acknowledgement.

15. The method of claim 14 further comprising:
in response to the notification of the failure to receive the acknowledgement, sending, via the computerized notification component, an emergency message to each of the at least one network access device.

16. A patient notification system, comprising:
a notification server;
an account information database;
an authentication server;
at least one network access device associated with at least one patient, each of the at least one network access device being communicably connectable to a display device; and
a scheduling server,
wherein the account information database is operative, in response to the patient opting-in to a notification program, to store personalized information pertaining to each of the at least one patient, the personalized information including (1) a unique identification code for the patient, (2) a predetermined reference number for the network access device associated with the patient, and (3) addressable information for the network access device, the opting-in of the patient to the notification program including electing to receive a perceptible notification via the network access device,
wherein the authentication server is operative:
to obtain the personalized information from the account information database;
to securely provide (1) the unique identification code for the patient, (2) the predetermined reference number for the network access device, and (3) the addressable information for the network access device, to the notification server; and
to securely provide (1) the unique identification code for the patient, and (2) the predetermined reference number for the network access device, to the scheduling server,
wherein the scheduling server is operative to monitor for a scheduled time to take medication to occur, and, upon detection of the occurrence of the scheduled time, to securely send, to the notification server, a first message containing (1) the unique identification code for the patient, and (2) the predetermined reference number for the network access device associated with the patient, wherein the notification server is operative, upon receipt of the unique identification code and the predetermined reference number from the scheduling server, to securely send, over at least one network, a notification message to the network access device in accordance with the addressable information for the network access device, wherein the network access device is operative, in response to receipt of the notification message, to cause the perceptible notification of the scheduled time to take the medication to be presented to the patient on the display device, and wherein the notification server is further operative to receive, over the at least one network, an acknowledgement of the patient having taken the medication from a selected one of the at least one network access device;

wherein the network access device is a set top box, wherein the at least one network includes one or more of a cable television (CATV) network and an Internet protocol television (IPTV) network, and wherein the sending of the notification message includes sending the notification message to the set top box over one or more of the CATV network and the IPTV network.

17. The system of claim 16, wherein the notification server is further operative to receive the acknowledgement of the patient having taken the medication from the network access device over one or more of the CATV network and the IPTV network.

18. The system of claim 16 wherein the notification server and the scheduling server are implemented on one or more computers or computerized devices.

19. A method of providing one or more notifications to, and receiving one or more acknowledgements from, a patient with regard to taking medication at least one scheduled time, comprising:

in response to the patient opting-in to a notification program:

obtaining personalized information pertaining to the patient, the personalized information including (1) a unique identification code for the patient, (2) a predetermined reference number for each of at least one network access device associated with the patient, and (3) addressable information for the network access device, the network access device being communicably connectable to a display device, the opting-in of the patient to the notification program including electing to receive the one or more notifications via the network access device; and storing the personalized information in an account information database;

obtaining, by a computerized authentication component, the personalized information from the account information database;

securely providing, by the computerized authentication component, (1) the unique identification code for the patient, (2) the predetermined reference number for the network access device, and (3) the addressable information for the network access device, to a computerized notification component;

securely providing, by the computerized authentication component, (1) the unique identification code for the patient, and (2) the predetermined reference number for the network access device, to a computerized scheduling component;

monitoring, by the computerized scheduling component, for the scheduled time to take the medication to occur;

upon detection of the occurrence of the scheduled time, securely sending, by the computerized scheduling component to the computerized notification component, a first message containing (1) the unique identification code for the patient, and (2) the predetermined reference number for the network access device associated with the patient;

upon receipt of the unique identification code and the predetermined reference number from the computerized scheduling component, securely sending, by the computerized notification component over at least one network, a notification message to the network access device in accordance with the addressable information for the network access device;

in response to receipt of the notification message at the network access device, causing, by the network access device, a perceptible notification of the scheduled time to take the medication to be presented to the patient on the display device; and receiving, at the computerized notification component over the at least one network, an acknowledgement of the patient having taken the medication from a selected one of the at least one network access device;

wherein the network access device is a set top box, wherein the at least one network includes one or more of a cable television (CATV) network and an Internet protocol television (IPTV) network, and wherein the sending of the notification message includes sending the notification message to the set top box over one or more of the CATV network and the IPTV network.

20. The method of claim 19 wherein the securely sending of the first message includes securely sending, to the computerized notification component, the first message containing the predetermined reference numbers for the respective patient notification devices configured as one or more of a mobile device, a network access device, and an intelligent home gateway.

* * * * *